United States Patent [19]

Gong et al.

[11] 4,332,903

[45] Jun. 1, 1982

[54] MEDIA MANIPULATION FOR PREPARING BIOLOGICALLY ACTIVE HOLLOW MYCELIAL PELLETS

[75] Inventors: Cheng-Shung Gong; Li-Fu Chen; George T. Tsao, all of West Lafayette, Ind.

[73] Assignee: Purdue Research Foundation, West Lafayette, Ind.

[21] Appl. No.: 174,455

[22] Filed: Aug. 1, 1980

[51] Int. Cl.³ .............................................. C12N 1/14
[52] U.S. Cl. .................................. 435/254; 435/931; 435/939
[58] Field of Search ........................ 435/254, 931, 939

[56] References Cited

U.S. PATENT DOCUMENTS 3,734,831  5/1973  Hulme .................................. 435/254
3,836,432  9/1974  Shimizu et al. ...................... 435/276

OTHER PUBLICATIONS

The Filamentous Fungi–Smith et al., vol. III Wiley N.Y., 1978, pp. 428, 450 and The Filamentous Fungi–Smith et al., vol. I, Wiley N.Y., 1975, pp. 259, 263. Canadian Journal of Microbiology vol. 8, pp. 133–136 (1962)-Clark.

Primary Examiner—Hiram Bernstein
Attorney, Agent, or Firm—Cushman, Darby & Cushman

[57] ABSTRACT

Biologically active hollow fungal mycelial pellets are prepared by media manipulation. Initially fungal spores are innoculated under conditions limiting growth to formation of tiny cell aggregates of less than about 2 mm. Thereafter, the aggregates are subjected to conditions supportive of vigorous vegetative growth and agitation to produce hollow pellets having a porous spherical webbed mycelial layer and hollow core.

5 Claims, No Drawings

MEDIA MANIPULATION FOR PREPARING BIOLOGICALLY ACTIVE HOLLOW MYCELIAL PELLETS

BACKGROUND OF THE INVENTION

The invention relates generally to the art of biological catalytic reactor systems with mycelia of fungi and more particularly to hollow mycelial pellets for biocatalytic conversions as well as the preparation of biologically active hollow mycelia pellets from mycelial fungi and preferably of the genus Rhizopus and Mucor.

Mycelial fungi have long been employed in the biocatalytic conversion of organic compounds. Thus, the breakdown of various carbohydrates has to some degree involved the use of fungi, but the use of fungi has been generally limited to an unsupported vegetative mass.

The use of mycelial fungi in biocatalytic systems is limited due to the difficulty in handling such masses. It is known that some mycelial fungi can form mycelial pellets in a conventional shaking culture as described by D. S. Clark, Canadian Journal of Microbiology Volume 8, 133–136 (1962). While such a pellet form is more desirable than the unshaped vegatative mass, not all forms of mycelial fungi are capable of forming such a pellet under conventional methods.

Accordingly, it is the primary object of the present invention to provide a method for preparing hollow mycelial fungal pellets by means of a media manipulation.

It is a further object of the present invention to provide an improved means for carrying out the biocatalytic conversions of organic compounds.

Still yet a further object of the present invention is to provide Rhizopus and Mucor mycelial hollow pellets having an outer surface of structural integrity. These and other objects of the present invention will become more apparent from the discussion which follows.

DETAILED DESCRIPTION OF THE INVENTION

When fungi grow in a liquid medium, their mycelia form a loose cotton-like mass. Some mycelial fungi can form pellets when they are grown in a circular action shaking incubator. The formation of pellet increases the cell density and facilitates the separation of the cell mass from the liquid products. Unfortunately not every fungus is able to form such mycelial pellets in a circular action shaking incubator. It is desirable to prepare the mycelia in a pellet form for use in a fermentation process, especially in a continuous fermentation process. In a continuous fermentation process, the flow properties and the cell density would determine the efficiency of the fermentation process.

The present invention provides a method for the preparation of fungal mycelial pellets from all types of mycelial fungi. Those fungi which are incapable of forming mycelial pellets in conventional shaking cultures can form mycelial pellets by the present method.

The pellets thus prepared exhibit enhanced flow properties when they are packed in a continuous fermentation reactor as compared to a packed mass of mycelia. The diffusion of the nutrients and the products into and out of the conventional mycelial pellets is rather slow. The fungal mycelial pellets prepared by the present invention grow into round hollow pellets with 0.5 to 5 mm and preferably 1-3 mm wall thickness of mycelium. The hollow pellets with thin webbed structured mycelial walls allow easy diffusion of nutrients into the pellets and the products out of the pellets.

The fungal mycelial pellets prepared according to this invention have a mycelial wall with a highly texturized structure which is resistant to shear force. The mycelial pellets prepared by conventional method have loose mycelial structure that would be sheared off at high flow rates experienced in a continuous reactor.

Mycelial pellets can of course be prepared by growing the culture in a full strength media solution in a circular shaking incubator, but as noted not every species of fungi is capable of forming mycelial pellets by this conventional method, for example, Mucor sp and Rizopus sp do not appear to form mycelial pellets under the conventional conditions.

Also, mycelial pellets when prepared by conventional methods are usually in a very loose form, i.e., they are like small cotton balls and are fragile. Such pellets can be broken easily by agitation. Thus, when gas is produced in the fermentation process, these loose mycelial pellets trap the gas and float on the top of the liquid medium and this causes mass transfer problems. Therefore, a hollow form of mycelial pellets is desirable to reduce the mass transfer barrier.

According to the present invention, there is also provided a means of producing biologically active hollow fungal mycelial pellets by media manipulation. The procedure generally is:

1. The fungi are innoculated into a medium solution which contains limited amount of growth factors such as nitrogen source, carbon source or trace metals and temperature.
2. Let the organism grow in an incubator. Because of the limited amount of nutrients only a very tiny amount of cell aggregates were developed.
3. Add the limited growth factors into the medium, then incubate them in an incubator. The tiny cell aggregates then acts like a nucleus; the continuous growth of mycelium of the organism developed into a mycelial pellet. Some fungal species are able to form hollow pellets. The mycelial pellets thus prepared usually have a mycelial wall which is highly texturized.

In general, the process for preparing biologically active hollow fungal mycelial pellets by media manipulation involves the steps of:

(a) innoculating a medium solution with mycelia fungal spores, said medium solution containing a limited amount of nutrient sufficient to support the growth of said spores to form tiny cell aggregates having a diameter of less than about 2 mm (generally ranging from about 0.5 to about 1.5 mm);

(b) incubating the innoculated solution under conditions to limit the vegetative growth of said spores to a diameter of less than 2 mm, and agitation (e.g. in a circular shaking incubator) until said spores form said aggregates;

(c) adding to the aggregates further nutrient to support vigorous vegetative growth of mycelia; and (d) incubating the aggregate under agitation (e.g., in a circular shaking incubator) for a period of time sufficient to allow the mycelium of the fungus to develop a porous spherical mycelial webbed sheath thereby forming a hollow fungal mycelial pellet.

Generally, the hollow core may range from about 0.5 mm to 1 cm in diameter with the webb thickness ranging from about 0.5 mm to 5 mm.

The following materials and procedures were employed in evaluating the present invention.

Isolation and Maintenance of the Mucoraceous Fungi

Several Chinese yeast preparations were obtained from various locations on the island of Taiwan. The dry circular cake of Chinese yeast cultures was first cracked and broken into a fine powder. This powder was suspended in sterile water and plated onto potato dextrose agar (PDA) plates containing 0.2% rose-bengal (Sigma). Rose-bengal inhibits the growth of yeasts and bacteria, but it inhibits the growth of fast-growing molds to a lesser extent. The PDA rose-bengal plates were incubated at 30° C. for 48 hours before the mycelial edge of a fungal colony was transferred. Single sporangiospores were then isolated. Several isolates were identified as Rhizopus species, and the rest were identified as Mucor species.

Cultures were maintained at 4° C. on PDA slants and transferred monthly.

Inoculum and Cultural Conditions

Both growing and non-growing mycelial systems were used. The growing mycelial system was prepared in the following manner: Small amounts of sporangiospore suspension were inoculated into 250 ml. Erlenmeyer flasks containing 100 ml of basic salts medium (BSM) consisting of 2.0 gm. $KH_2PO_4$, 1.4 gm $(NH_4)_2SO_4$, 0.3 gm. urea, 0.3 gm $CaCl_2$, 0.3 gm. $MgSO_4.7H_2O$, 1.0 gm. peptone (Difco), 10.0 gm. either glucose or xylose, 1.0 mg. $Fe^{++}$, 0.5 mg. $Mn^{++}$, 0.8 mg. $Zn^{++}$, and 0.5 mg. $Co^{++}$, each per liter of culture medium, and finally 0.011 M in sodium citrate buffer, pH 5.8. These cultures were incubated at 30° C. overnight on a reciprocal shaker and then harvested by filtration.

The non-growing mycelial system was set up as follows:

Fresh mycelia, harvested from the growing mycelial system, were introduced into a 250 ml. Erlenmeyer flask containing 100 ml. of BSM with either 20.0 gm. glucose, or 10 gm. xylose per 100 ml., and incubated at 30° C. in a New Brunswick psycrotherm incubator shaker. These cultures were kept under nitrogen gas for the appropriate period of time. Unless otherwise indicated, sugars and BSM broth were autoclaved separately and mixed before inoculation.

The following examples are offered in order to more fully describe the invention, but are not to be construed as limiting the scope thereof.

EXAMPLE 1

Rizopus spores were incubated in a liquid basic salt medium for two days. The basic salt medium was depleted with carbon source, pH 4.5.

The resultant growth of Rizopus was in the form of tiny cell aggregates. After glucose was added to the medium, mycelial pellets were formed.

EXAMPLE 2

Rizopus spores were incubated in a liquid basic salt medium as in Example 1, except that glucose was added and the pH was 3.0. After two days, tiny cell aggregates developed and the pH was then adjusted to pH 4.5. After incubation for two days, hollow core mycelial pellets were formed.

EXAMPLE 3

Spores of Mucor sp were used to replace Rizopus spores in Example 1. The resulting mycelial pellets which developed were not hollow inside.

EXAMPLE 4

The production of ethanol from xylose, xylan and hemicellulose hydrolyzate by Mucor sp was carried out using D(+) xylose and Larchwood xylan obtained from Sigma Chemical Company and hemicellulose hydrolyzate.

The mycelia were obtained from cells grown in basic-salt medium (BSM) and were inoculated into the BSM with carbon sources as indicated in Table 1. The mycelia were incubated at 30° C. for a period of four days. The results are shown in Table 1. Soluble sugars from hemicellulose hydrolyzate were measured by reducing sugar methods.

TABLE I

| Ethanol Production by Mucor sp. | | |
|---|---|---|
| Carbon Source (%) | | (%) EtOH W/V |
| Xylose | 8 | 3.8 |
| Xylan | 5 | 0.6 |
| Hemicellulose hydrolysate | 5.8 | 2.4 |

The invention, in its broadest aspects, is not limited to the specific details shown and described, but departures may be made from such details within the scope of the accompanying claims without departing from the principles of the invention. Furthermore, the invention may comprise, consist, or consist essentially, of the hereinbefore recited materials and steps.

What is claimed is:

1. A process for the preparation of biologically active hollow fungal mycelial pellets having an outer surface of structural integrity which comprises the steps of:
    (a) innoculating a medium solution with mycelia fungal spores, said medium solution containing a limited amount of nutrient sufficient only to support the growth of said spores to form tiny cell aggregates having a diameter of less than about 2 mm;
    (b) incubating the innoculated solution under conditions to limit the vegetative growth of said spoes to a diameter less than 2 mm until said spores form said aggregates;
    (c) adding to the aggregates further nutrient to support vigorous vegetative growth of the mycelia; and
    (d) incubating the aggregates under agitation for a period of time sufficient to allow the mycelia of the fungi to develop a porous spherical webbed mycelial layer thereby forming a hollow fungal mycelial pellet having an outer surface of structural integrity.

2. A process according to claim 1 wherein said spores are from the genus Rhizopus or Mucor.

3. A process according to claim 1 wherein said nutrient is glucose.

4. Biologically active hollow fungal mycelial pellets produced according to the method of claim 1 wherein the fungal spores are incapable of forming mycelial pellets in conventional shaking cultures.

5. Biologically active hollow fungal mycelial pellets produced according to the method of claim 2.

* * * * *